(12) United States Patent
Freeman et al.

(10) Patent No.: US 9,198,633 B2
(45) Date of Patent: Dec. 1, 2015

(54) COMPUTED TOMOGRAPHY PERFUSION PHANTOM AND METHOD USE THEREOF

(75) Inventors: Kenneth L. Freeman, Stow, OH (US); Stephen P. Dechant, Lodi, WI (US)

(73) Assignee: Gammex, Inc., Middleton, WI (US)

( * ) Notice: Subject to any disclaimer, the term of this patent is extended or adjusted under 35 U.S.C. 154(b) by 31 days.

(21) Appl. No.: 13/985,179

(22) PCT Filed: Jul. 27, 2012

(86) PCT No.: PCT/US2012/048664
§ 371 (c)(1),
(2), (4) Date: Aug. 13, 2013

(87) PCT Pub. No.: WO2013/019666
PCT Pub. Date: Feb. 7, 2013

(65) Prior Publication Data
US 2014/0133636 A1 May 15, 2014

Related U.S. Application Data

(60) Provisional application No. 61/513,288, filed on Jul. 29, 2011.

(51) Int. Cl.
*A61B 6/00* (2006.01)
*A61B 6/03* (2006.01)

(52) U.S. Cl.
CPC ............... *A61B 6/583* (2013.01); *A61B 6/032* (2013.01); *A61B 6/481* (2013.01); *A61B 6/504* (2013.01); *A61B 6/507* (2013.01)

(58) Field of Classification Search
CPC .......... A61B 6/00; A61B 6/032; A61B 6/481; A61B 6/504; A61B 6/507; A61B 6/583; G06K 9/00; G12B 13/00
USPC ............ 378/18, 65, 207; 250/252.1; 382/131, 382/132
See application file for complete search history.

(56) References Cited

U.S. PATENT DOCUMENTS 4,331,869 A 5/1982 Rollo
5,808,468 A * 9/1998 Bis et al. ........................ 324/318
(Continued)

FOREIGN PATENT DOCUMENTS

WO 2007081662 A2 7/2007
WO 2010089699 A2 8/2010
WO WO 2010089699 A2 * 8/2010 ............... A61B 6/00

OTHER PUBLICATIONS

Chong et al., Separation of bone from iodine- and gadolinium-based contrast agents using dual energy CT, Mar. 2008, Physics of Medical Imaging, Proc. of SPIE vol. 6913, p. 1, 3.*
(Continued)

*Primary Examiner* — Irakli Kiknadze
*Assistant Examiner* — Julio M Duarte-Carvajalino
(74) *Attorney, Agent, or Firm* — Andrus Intellectual Property Law, LLP

(57) ABSTRACT

A computed tomography perfusion phantom includes a scanned plane configured to align with an imaging plane of a CT device. A sample rod extends through the scan plane and includes a plurality of adjacent cells. The plurality of adjacent cells are each constructed of materials having predetermined CT numbers and the plurality of adjacent cells include cell of a plurality of CT numbers. A drive motor is coupled to the sample rod and the drive motor moves the sample rod through the scan plane. A method of calibrating a CT device with the perfusion phantom includes aligning the scan plane of the perfusion phantom with an imaging plane of the CT device. The drive motor moves the sample rod through the scan plane of the perfusion phantom. A plurality of CT number measurements of the sample rod are acquired through the scanned plane of the perfusion phantom.

20 Claims, 8 Drawing Sheets

(56) References Cited

U.S. PATENT DOCUMENTS

| | | | |
|---|---|---|---|
| 6,205,871 | B1 | 3/2001 | Saloner et al. |
| 6,224,257 | B1 | 5/2001 | Launay et al. |
| 6,314,313 | B1 | 11/2001 | Romeas et al. |
| 7,010,082 | B2 | 3/2006 | Hein et al. |
| 7,125,166 | B2 | 10/2006 | Eck et al. |
| 7,151,253 | B2 | 12/2006 | Varchena et al. |
| 7,569,809 | B2 | 8/2009 | Vija et al. |
| 7,699,522 | B2 | 4/2010 | Varchena |
| 7,728,285 | B2 | 6/2010 | Suh et al. |
| 7,842,929 | B2 | 11/2010 | Krautim et al. |
| 2003/0063704 | A1* | 4/2003 | Lang ............ 378/54 |
| 2005/0111722 | A1* | 5/2005 | Gerwin ............ 382/132 |
| 2008/0167552 | A1 | 7/2008 | Bouchevreau et al. |
| 2008/0192892 | A1* | 8/2008 | Dilmanian et al. ............ 378/65 |
| 2008/0310582 | A1 | 12/2008 | Flohr et al. |
| 2009/0202035 | A1* | 8/2009 | Tsukagoshi ............ 378/8 |
| 2009/0316972 | A1 | 12/2009 | Borenstein et al. |
| 2010/0288916 | A1 | 11/2010 | Cho et al. |
| 2011/0062318 | A1 | 3/2011 | Bisaillon et al. |

OTHER PUBLICATIONS

International Preliminary Report on Patentability, PCT International Application No. PCT/US2012/048664, mailed Feb. 13, 2014.

International Search Report, PCT International Application No. PCT/US2012/048664, mailed Oct. 5, 2012.

* cited by examiner

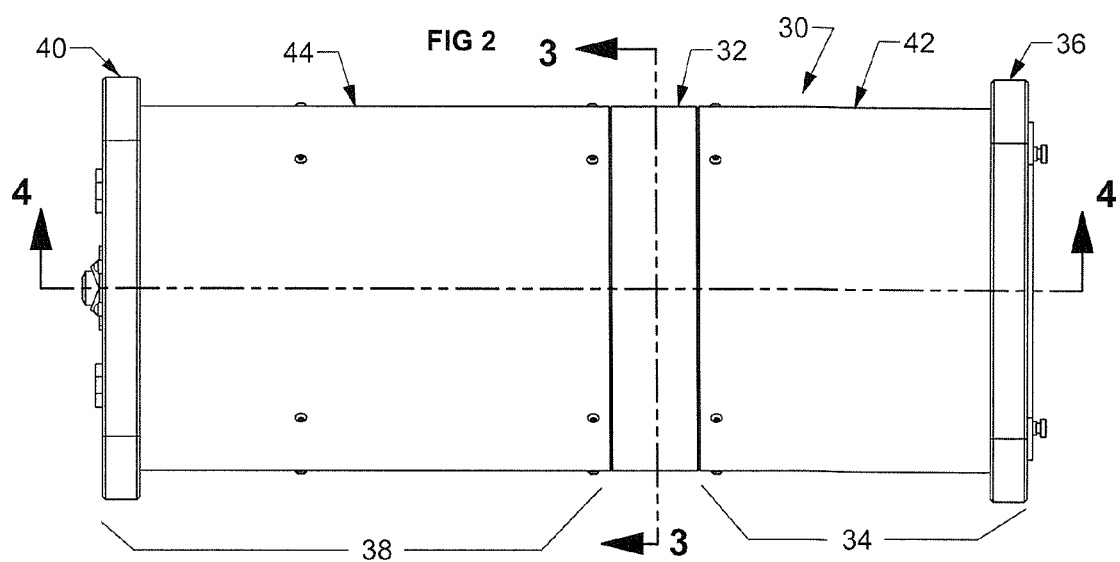
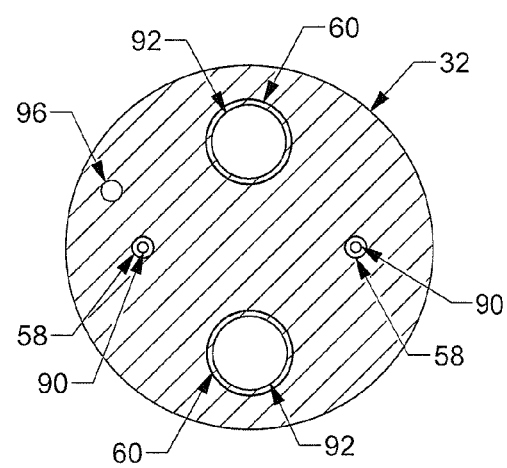

COMPUTED TOMOGRAPHY PERFUSION PHANTOM AND METHOD USE THEREOF

CROSS-REFERENCE TO RELATED APPLICATIONS

This application is the U.S. national stage application of International Application PCT/US2012/048664, filed. Jul. 27, 2012, which international application was published on Feb. 7, 2013, as International Publication WO 2013/019666 in the English language. The International Application claims priority of U.S. Provisional Patent Application 61/513,288, filed Jul. 29, 2011. Both applications are hereby incorporated by reference in their entireties.

BACKGROUND

The present disclosure is related to the configuration and calibration of a computed tomography (CT) device using a phantom. More specifically, the present disclosure is related to a perfusion phantom and a method of using the perfusion phantom for CT device calibration.

Bodies of material that represent a quantity of one or more body structures are known as phantoms. Phantoms represent one or more characteristics or properties (e.g. mass, composition, dimension, shape, magnetic, or radiation) of one of more body parts or structures. Such phantoms are used in the medical field for quality control of medical imaging and radiotherapy devices. Such testing can be a part of initial set up and calibration, or can be used as part of a routine quality assurance program to maintain optimal system performance. The American College of Radiology (ACR) offers a voluntary program of CT device quality assurance that includes the use of phantoms for CT device accreditation.

The human body is a dynamic subject that is constantly moving and moreover, many diagnostic imaging procedures rely upon the evaluation of dynamically changing conditions within a patient's body. One such technique that is used with CT imaging devices is to introduce a contrast agent to the patient, organ, or organ system that is to be imaged, and using the CT device to track the progression of the contrast agent through the region of interest (ROI).

Phantoms, which are typically static structures, are challenged in quality assurance and calibration applications for CT devices used to capture dynamically changing images.

BRIEF DESCRIPTION OF THE DRAWINGS

FIG. 2 is a side view of an embodiment of a perfusion phantom.

FIG. 3 is a cross sectional view of an embodiment of a perfusion phantom taken along plane 3 of FIG. 1 and line 3-3 of FIG. 2.

DETAILED DISCLOSURE

Medical imaging applications seek to provide visual representations of bodily structures, organs, and organ systems. Computed tomography (CT) is one known platform for diagnostic imaging. While CT will exemplarily be used throughout the current description, it will be understood by one of ordinary skill in the art that medical imaging devices may include other modalities of imaging devices used in the medical field.

One type of procedure that may be performed with a CT device is a blood perfusion analysis. Perfusion analysis evaluates an organ or tissue-region for the flow and/or distribution of blood (perfusion) within the targeted organ, or tissue-region by examining the blood flow in the vessels feeding the organ or tissue-region.

In perfusion analysis, the patient is injected with a contrast material. Often, this contrast material is a radiopaque substance that stands out in radiographic images as compared to tissue and fluids commonly found in the body. As an example, the contrast material may be on iodinated compound. A region of interest (ROI) is scanned with the CT device multiple times in order to capture the distribution over time of the contrast material through the vessel, organ, or tissue-region being imaged.

As the perfusion analysis progresses, the amount of the contrast material first increases, then peaks, and is finally washed out of the vessel, organ, or tissue-region. This progression can be seen in the changing CT number for the ROI as obtained from an analysis of each of the progressive CT scans of the ROI.

Specific to each type of vessel, organ, or tissue-region selected to be the ROI for the perfusion analysis, the resulting time-density curve of the CT number of the ROI across progressive scans exhibit generalized graph curves or shapes that are associated with normal and abnormal perfusion through the vessel or tissue. Identified deviations from expected normal perfusion graph curves can provide diagnostic and therapeutic insight to trained healthcare professionals.

As disclosed herein, a CT perfusion phantom enables the calibration and continued quality assurance that the CT number time density curves obtained from a CT apparatus during a perfusion analysis are accurate.

Figure 1:
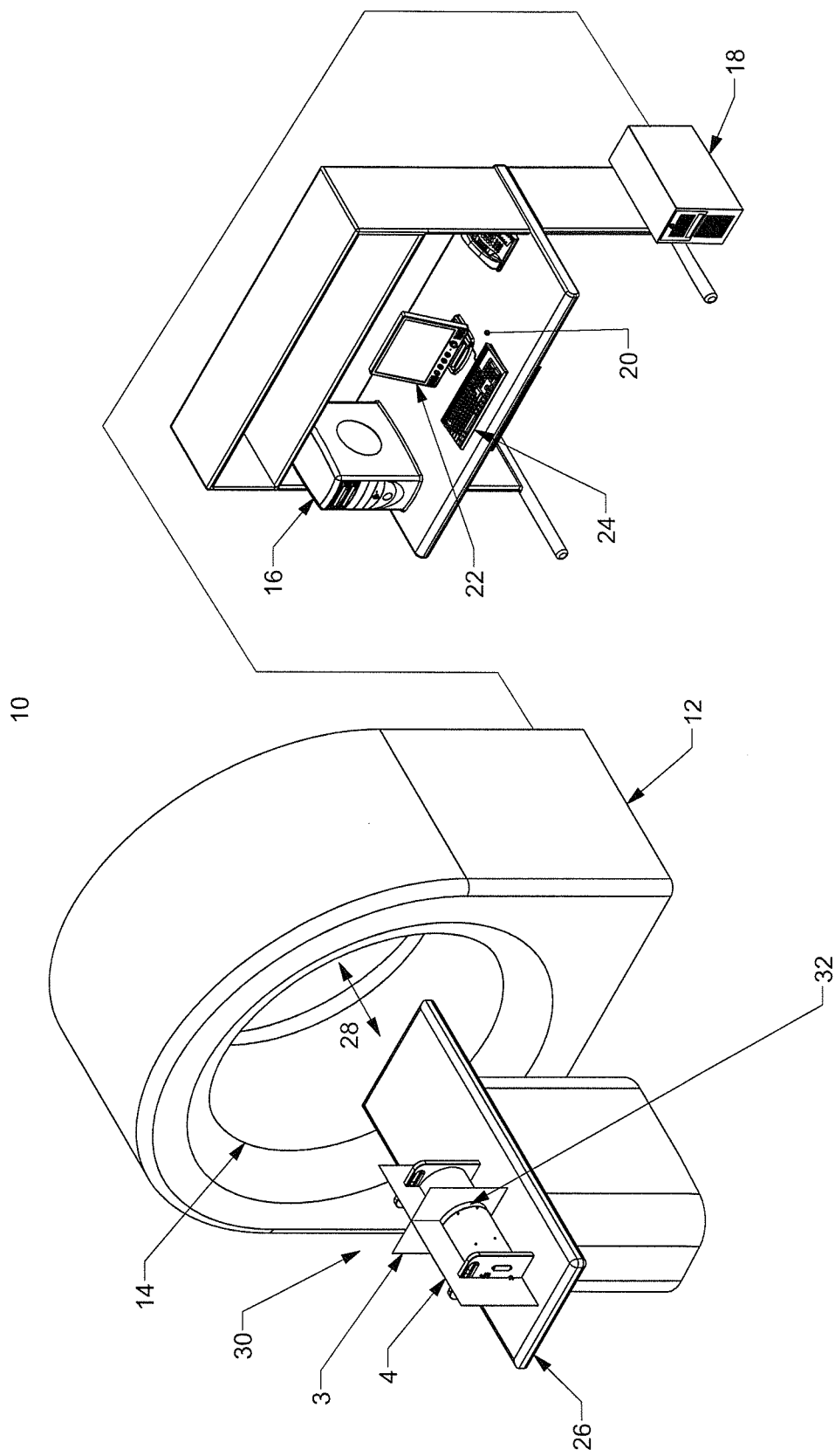
FIG. 1 is a system diagram depicting an embodiment of a phantom in use with a CT device.

FIG. 1 depicts a medical imaging system 10. The medical imaging system 10 includes a computed tomography (CT) device 12. The CT device 12 includes one or more x-ray radiation sources (not depicted) that rotate about a defined path. The radiation sources are supported by a circular gantry 14 or a C-arm (not depicted).

The CT device 12 is communicatively connected to a computer 16 or another processing unit. In one embodiment, the computer 16 is integrated with the CT device 12 and in an alternative embodiment, the computer 16 is a separate component that is communicatively connected such as with wired or wireless communication platforms. The computer 16 executes computer readable code that is either stored locally or at a remote computer storage location, such as a server 18 that is communicatively connected to the computer 16 by wired or wireless communication networks.

The computer 16 executes the computer readable code to operate the CT device 12 in order to capture medical images in the manner directed by a clinician or other user through a user interface 20. The user interface 20 comprises a graphical display 22 that presents one or more graphical user interfaces (GUI) that present captured medical images or user input prompts, other medical or patient information, or a combination thereof. The user input device 20 further includes a data entry device 24 that is exemplarily a keyboard, mouse, or touch screen, or any other of a variety of data entry devices as would be recognized by one of ordinary skill in the art. In alternative embodiments, the computer 16, user interface 20, graphical display 22, and data entry device 24 can be integrated into any of a variety of devices, such as, but not limited to desktop computers, laptop computers, tablet computers, or mobile computers/smartphones.

The medical imaging system 10 further includes a movable gurney 26. The movable gurney 26 is configured to support a patient or other subject for imaging by the CT device 12. The movable gurney 26 translates along arrow 28 to position the subject within the gantry 14. Additionally, the movable gurney 26 can be movable along additional axes, including but not limited to four degrees of freedom movement. The positioning of the subject within the gantry 14 on the gurney 26 aligns a particular region of interest (ROI) of the subject with an imaging plane of the one or more radiation sources of the CT device 12. The one or more radiation sources of the CT device 12 each produce image slices through the subject along the imaging plane. The translation of the movable gurney 26 changes the ROI of the patient that is imaged by the CT device. An embodiment of the perfusion phantom 30 is depicted as being placed on the movable gurney 26. While embodiments of the perfusion phantom 30 will be described in further detail herein, the perfusion phantom 30 includes a scan plane 32. In use of the perfusion phantom 30, the movable gurney 26 is translated generally along arrow 28 in order to align the scan plane 32 of the perfusion phantom 30 with the imaging plane of the radiation sources of the CT device 12.

FIG. 2 is a side view of an embodiment of a perfusion phantom. The perfusion phantom 30 includes a CT end 34 that extends between the scan plane 32 and a CT end handle 36. The perfusion phantom 30 further includes a drive end 38 that extends between the scan plane 32 and a drive end handle 40. In an embodiment, the perfusion phantom 30 is oriented on the gurney 26 (FIG. 1) in a manner such that the CT end 34 extends into the CT device 12 past the imaging plane of the CT device 12. However, it is understood that these designations are used for descriptive purposes and it will be recognized by one of ordinary skill in the art that embodiments of the perfusion phantom 30 can be designed to have alternative orientations with respect to a CT device 12.

The handles 36 and 40 facilitate the movement and proper placement of the phantom 30 on the gurney by a technician. The handles 36 and 40 further form the opposing ends of the perfusion phantom 30. The handles 36 and 40 also provide structural support to the phantom 30. A CT end outer tubular cover 42 extends from the CT end handle 36 to the scan plane 32. A drive end outer tubular cover 44 extends from the drive end handle 40 to the scan plane 32. The outer tubular covers 42 and 44 further provide structural integrity to the perfusion phantom 30 as well as protect the operational elements of the perfusion phantom 30 contained within. The outer tubular covers 42 and 44 define a CT end open interior 46 and a drive end open interior 48 (FIG. 4), respectively, on either side of the scan plane 32 between the scan plane 32 and a respective handle 36 or 40. The outer tubular covers 42 and 44 may be visually transparent or opaque in construction, as outer covers 42 and 44 of a transparent material will permit the viewing of the elements within the perfusion phantom 30 by a user which may facilitate a basic user confirmation that the perfusion phantom 30 has been assembled correctly as disclosed in further detail herein.

Figure 4:
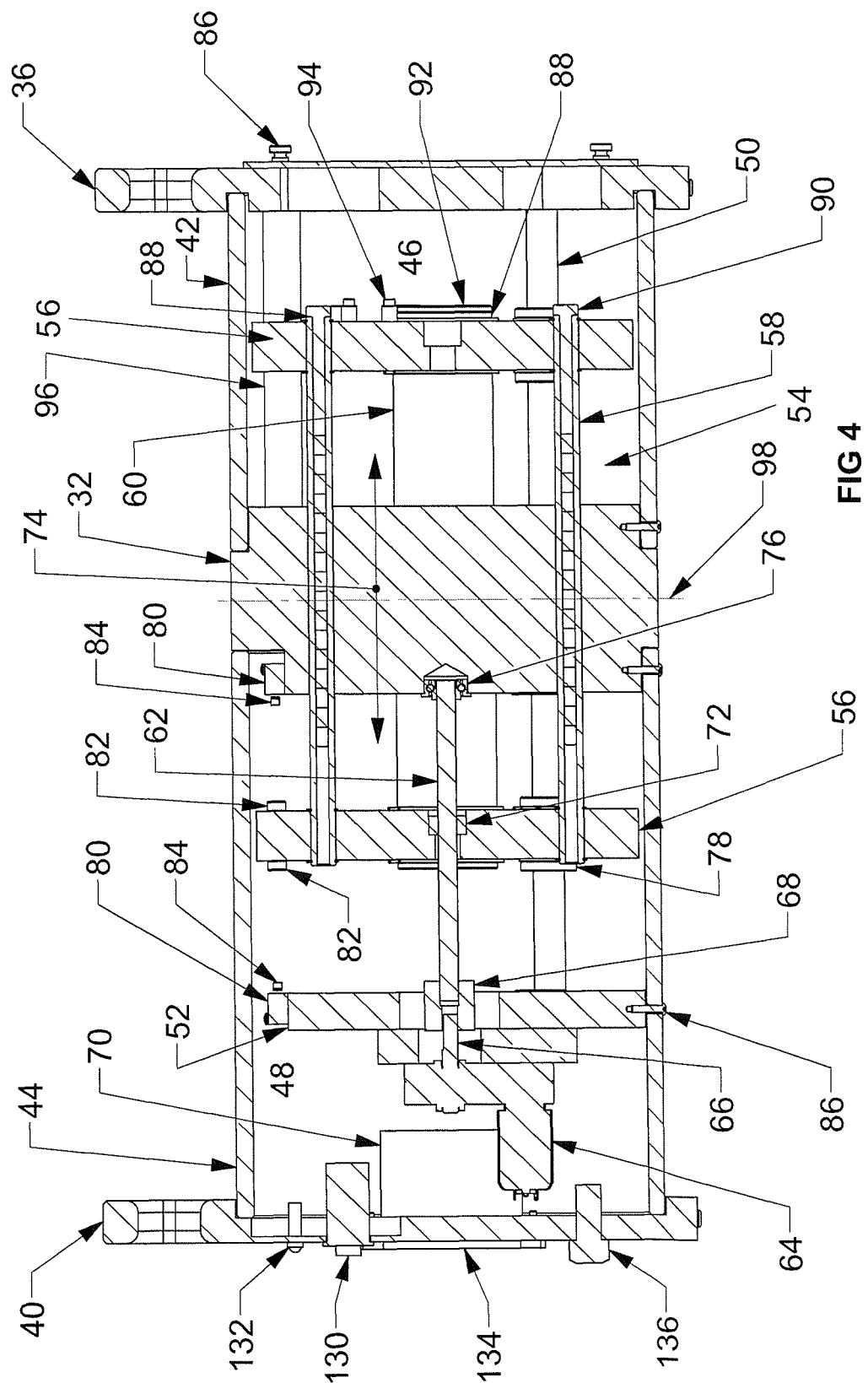
FIG. 4 is a cross sectional view of an embodiment of a perfusion phantom taken along plane 4 of FIG. 1 and line 4-4 of FIG. 2.

FIG. 3 is a cutaway slice view of an embodiment of the perfusion phantom 30 as taken along plane 3 of FIG. 1 and line 3-3 of FIG. 2. FIG. 4 is a cutaway view of the perfusion phantom 30, as take along plane 4 of FIG. 1 and line 4-4 of FIG. 2. It is understood that as the views of the perfusion phantom 30 in FIGS. 3 and 4 are different views of the same embodiment, that like reference numerals between FIGS. 3 and 4 identify the same structures and that the following description is in reference to FIGS. 3 and 4.

Referring specifically to FIG. 4, a rail 50 extends from either side of the scan plane 32 through the open interiors 46 and 48. A rail 50 extends from the CT end handle 36 to the scan plane 32. A rail 50 extends from a drive support 52 on the drive end 38 to the scan plane 32. It is recognized that in embodiments, a plurality of rails 50 extending away from the scan plane 32 may be used.

A carriage 54 is defined between two opposed end plates 56. Sample tubes that extend between the end plates 56 provide structural support and linear dimension to the carriage 54. In the embodiment of the perfusion phantom 30 depicted, the carriage 54 includes at least one vessel sample tube 58 and at least one tissue sample tube 60. In the embodiment of the perfusion phantom 30 depicted in FIGS. 3 and 4, there are two vessel sample tubes 58 and two tissue sample tubes 60 as can be best seen in FIG. 3. However, it is to be understood that alternative embodiments may include other numbers of sample tubes. In the embodiment depicted, the sample tubes 58 and 60 are circular in cross section and the vessel sample tubes 58 differ in dimension from the tissue sample tubes 60. It will be recognized that in alternative embodiments, the sample tubes 58 and 60 may be constructed of alternative cross sectional shapes or sizes based upon material, necessity, or the specific tissue region, organ, or organ system to be modeled.

The carriage 54 is controllably positioned within the perfusion phantom 30 by a worm gear 62 that is driven by a motor 64. A drive shaft 66 of the motor 64 is operationally connected to the worm gear 62 by a coupling 68.

The motor 64 is exemplarily an electric motor that receives energization from a power supply 70 which is exemplarily a battery. Alternative embodiments include a power supply 70 that is a power cord coupling suitable to connect the perfusion phantom 30 to a suitable source of utility electricity. The motor 64 operates to turn the drive shaft 66 either in the clockwise or counterclockwise directions, such rotation is translated to the worm gear 62, which through nut 72 in the end plate 56, translates into linear motion of the carriage 54 in the direction of arrow 74. The end 76 of the worm gear 62 is rotatably coupled to the scan plane 32.

While the motor 64 has been described above as driving a worm gear 62, it will be understood by persons of ordinary skill in the art in view of this disclosure, that a variety of other styles and configurations of motors and drives may be incorporated into embodiments of the phantom as disclosed herein. Non-limiting examples of such motors and configurations include, but are not limited to a linear motor, a cable drive, or a linear actuator.

Bearings 78 in the end plates 56 facilitate sliding engagement between the end plates 56 and the rails 50. Thus, operation of the motor 64 can move the carriage 54 along the rail or rails 50 to move the carriage 54 between a first carriage position wherein a greater portion of the carriage 54 is located in the CT end 34 of the perfusion phantom 30, and a second carriage position wherein a greater portion of the carriage 54 resides in the drive end 38 of the perfusion phantom 30.

Limit switches 80 are respectively positioned on the drive support 52 and the scan plane 32. Arrestor pads 82 positioned on the end plate 56 interact with a respective sensor 84 of each of the limit switches 80. In one embodiment, the sensors 84 are pressure sensors that sense the impact of the arrestor pads 82 to indicate that the carriage 54 has reached one end of the translational path of the carriage 54. While described above as being a pressure sensor, it will be understood that in alternative embodiments, the sensor 84 may be mechanical, magnetic, electrical, or another type of sensor known to one of ordinary skill in the art. The arrestor pad 82 would similarly be selected such as to facilitate interaction with the type of sensor 84 in the embodiment.

Figure 5:
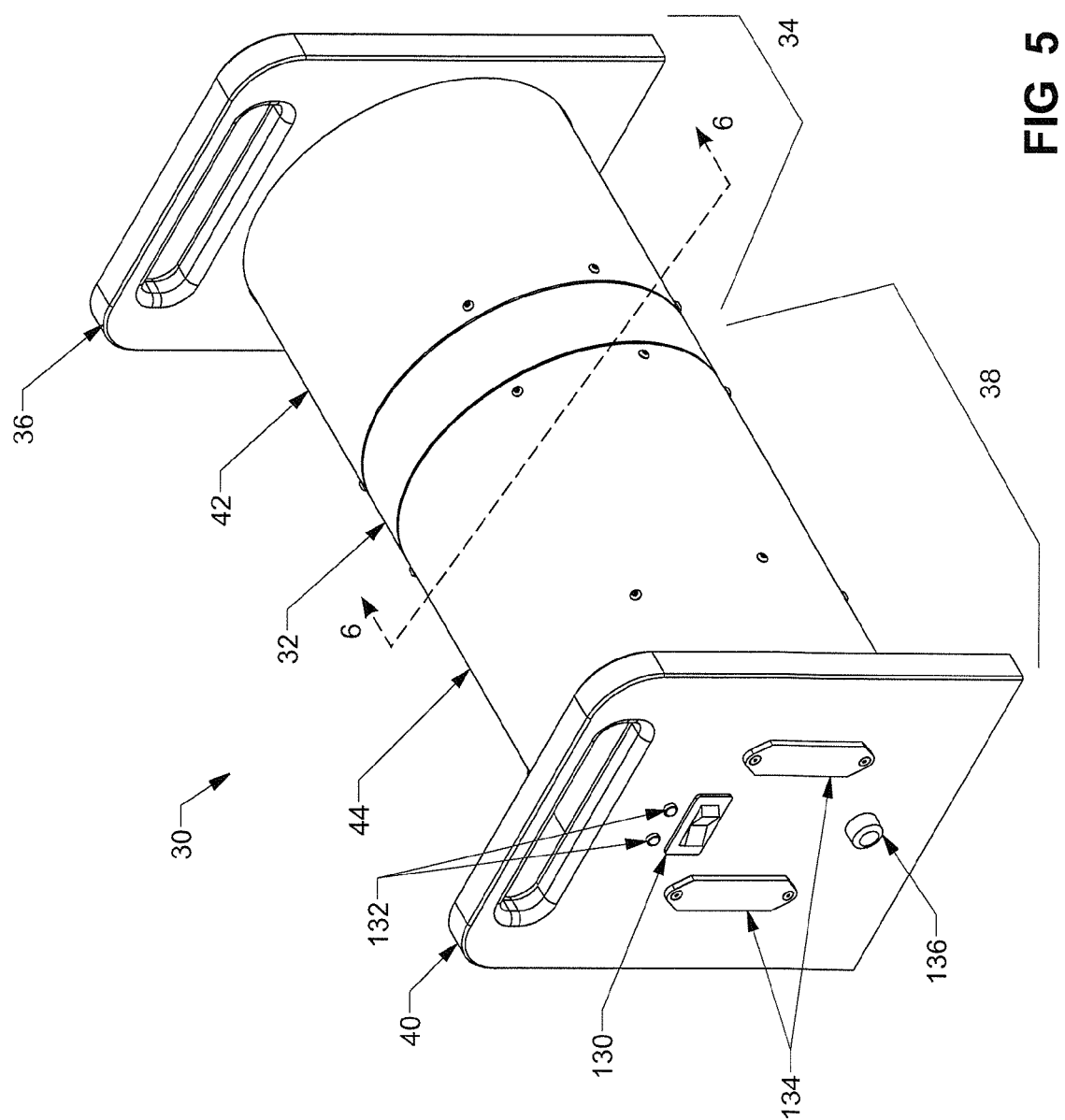
FIG. 5 is an isometric view of an embodiment of an assembled perfusion phantom.

FIG. 5 depicts an isometric view of an embodiment of the perfusion phantom 30. Particularly, FIG. 5 depicts the drive end handle 40 of the drive end 38 of the perfusion phantom 30. The controls for the perfusion phantom 30 are located in the drive end handle 40. A toggle switch 130 is operated by a clinician or technician between the positions of "forward"; "off"; and "reverse." It is with the toggle switch 130 that the clinician or technician controls the direction of the movement of the carriage 54 (FIG. 3) within the perfusion phantom 30. LED indicator lights 132 provide a visual feedback indication of the basic operation of the phantom, namely whether the carriage is being driven forward, reverse, or is off. Additional controls of the LED indicator lights 132, exemplarily blinking, can be used in embodiments to indicate a low battery or other maintenance and/or warning conditions.

It is to be understood that alternative embodiments, a more complex user interface that exemplarily includes a number pad (not depicted) or other input device and/or LCD display (not depicted) or other graphical display may be used in some embodiments, particularly in embodiments of the perfusion phantom as disclosed herein with more complex and/or more detailed control over the operation of the perfusion phantom.

The drive end handle 40 further includes battery slots 134 that are configured to receive and retain one or more batteries which, in embodiments, may be used as a power source for the perfusion phantom 30. The drive end handle 40 further includes a fuse slot 136 in which a fuse (not depicted) used for electrical isolation and protection of the components of the perfusion phantom is disposed.

Figure 6:
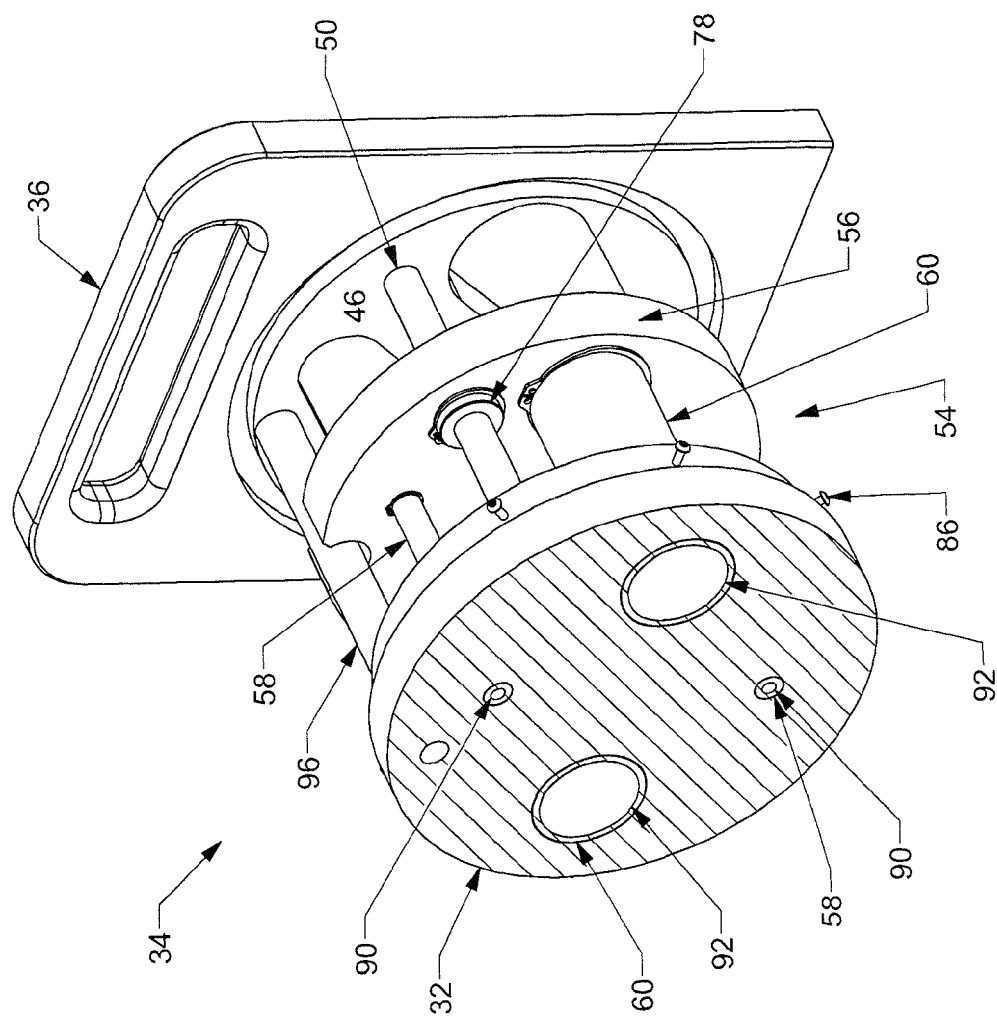
FIG. 6 is a cross sectional view of an embodiment of a perfusion phantom taken along line 6-6 of FIG. 5.

Referring back to—FIGS. 2 and 4, the perfusion phantom 30 is modularly constructed such that the phantom 30 can be at least partially disassembled for adjustment and maintenance of the components within the phantom 30. As such, the outer perimeter of the perfusion phantom 30 as defined by the handles 36 and 40 and the covers 42 and 44 are secured to the scan plane 32 and to the drive support 52 with the use of a plurality of fasteners 86, which may, in an exemplary embodiment, be screws as shown in FIGS. 4-6. In one particular embodiment, one or more screws 86 can be removed to separate the CT end handle 36 and the CT end tubular cover 42 from the perfusion phantom 30, thus exposing the CT end 34 of the components within the perfusion phantom 30. As shown in FIGS. 3 and 4, the vessel sample tubes 58 and the tissue sample tubes 60 each have open ends 88 at the CT end 34. The open ends 88 are configured such as to receive sample rods as will be described in further detail herein. As noted above, just as the vessel tubes 58 and the tissue sample tubes 60 may be of different sizes, shapes, or dimensions, the sample rods would similarly be constructed to a size, shape, and dimension to be received in one or more sample tubes. Specifically, vessel sample rods 90 are dimensioned to be received within the vessel sample tubes 58 and tissue sample rods 92 are dimensioned to be received within the tissue sample tubes 60. Retaining clips 94 secure the sample rods within the sample tubes 58 and 60. It is understood that while the retaining clips 94 have been depicted in the currently described embodiment, a person of ordinary skill in the art would recognize a variety of other suitable retaining solutions, including, but not limited to clips, clasps, friction fit, or screw fit retaining solutions that may also be used to secure the sample rods within the respective sample tubes 58 and 60.

As will be disclosed in greater detail herein, after the sample rods are secured within the respective sample tubes, the CT end tubular cover 42 and CT end handle 36 can be re-assembled to close the phantom 30 into a condition for use.

As will be described in further detail herein, the perfusion phantom 30 further includes a tube that can accept an ion chamber 96 that extends through the CT end 34 of the perfusion phantom 30 and at least partially through the scan plane 32. More specifically, the ion chamber 96, when within the holder, extends at least through a center line 98 of the scan plane 32. As will be described in further detail herein, the ion chamber 96 when inserted into the holder provides the functionality to the perfusion phantom 30 of the measurement of radiation dose during a calibration or quality assurance procedure with a CT device. This measurement of radiation dose during a calibration procedure can be used to tailor a procedure to minimize radiation dose delivered to a patient.

FIG. 6 is a sectional view of an embodiment of a perfusion phantom 30 without the CT and tubular cover 42, taken along line 6-6 of FIG. 5. FIG. 6 depicts in an isometric relation many of the features previously depicted and described with respect to FIGS. 3 and 4 above. In particular, FIG. 6 shows the tissue sample rods 92 disposed within the tissue sample tubes 60 and the vessel sample rod 90 that is disposed within the vessel sample tubes 58. As shown in FIG. 6, one of the vessel sample rods 90 can represent a vein while the other sample rod 90 represents an artery. The isometric view of FIG. 6 further helps to show the relationship of the fixed structures within the phantom 30, such as the ion chamber 96, scan plan 32, and the rail 50 in relation to the movable components of the carriage 54 that include the end plate 56, vessel sample tubes 58, and tissue sample tubes 60.

Figure 7:
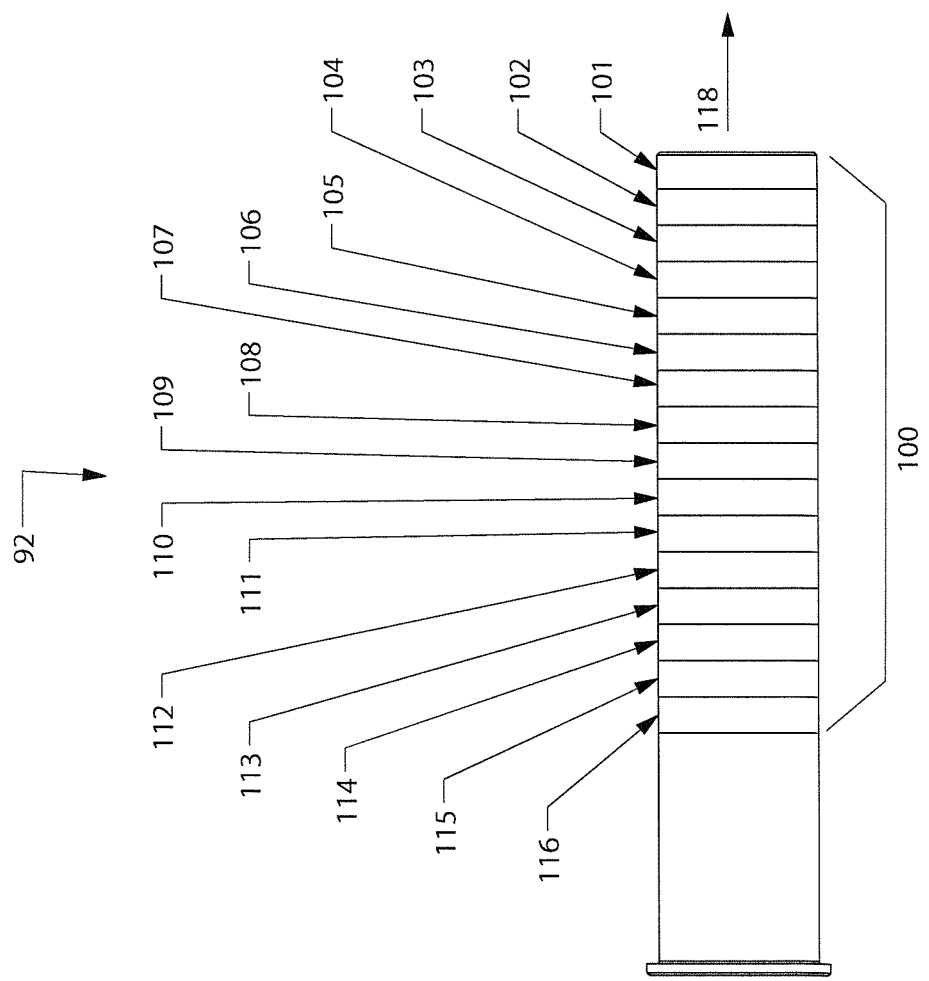
FIG. 7 depicts an embodiment of a sample rod assembly.

FIG. 7 depicts an exemplary embodiment of a sample rod as disclosed above with respect to the embodiment of the perfusion phantom 30. The sample rod depicted in FIG. 7 is exemplarily a tissue sample rod 92. However, it will be understood that the disclosure herein with respect to the tissue sample rod 92 is equally applicable to a vessel sample rod 90. The tissue sample rod 92 has a measurement region 100 which is defined by a plurality of sample cells 101-116. While the embodiment of the tissue sample rod 92 depicted in FIG. 7 includes sixteen sample cells, it is to be understood that this number of cells is merely exemplary and alternative embodiments of sample rods may include more or fewer sample cells. Each of the sample cells are constructed of a material with a CT number that is selected independently from the CT numbers of the other sample cells. Similarly, the CT numbers selected for the sample cells will depend upon whether the sample rod 92 is designed to represent a vessel such as an artery or a vein, or organ tissue, and further which organ or organ structure is to be represented by the sample rod. In exemplary embodiments, the tissue sample rod 92 represents a sample area of the brain.

The CT number of each of the sample cells 101-116 is selected to create a model perfusion graph when each of the cells 101-116 are sequentially scanned by a CT device. Thus, the change in the CT number across a sequential scan of the sample cells 101-116 represents the wash in and wash out of the contrast agent into the tissue, artery, or vein represented by the sample rod. In an embodiment, the sample rod is constructed of an epoxy material and the CT number is achieved in each of the cells by varying concentrations of additive substances to the epoxy. Two such additives are iodine and calcium. Increased concentrations of these materials within the cell will result in a cell that produces a higher CT scan result when imaged by a CT device.

In a still further embodiment, the shape, size, or diameter of the sample rod, or the sample cells within the sample rod, are designed to achieve a designated CT number or characteristic.

Table 1 provides exemplary CT numbers for exemplary sample cells for sample rods representing tissue, artery, or vein of a patient. The CT numbers are provided in Hounsfield units (HU).

| Cell Number | CT Number - Tissue | CT Number - Artery | CT Number - Vein |
| --- | --- | --- | --- |
| 101 | 35 | 30 | 75 |
| 102 | 35 | 30 | 80 |
| 103 | 35 | 450 | 85 |
| 104 | 35 | 700 | 100 |
| 105 | 35 | 800 | 150 |
| 106 | 40 | 600 | 400 |
| 107 | 50 | 250 | 700 |
| 108 | 55 | 150 | 900 |
| 109 | 60 | 100 | 600 |
| 110 | 55 | 100 | 300 |
| 111 | 45 | 90 | 300 |
| 112 | 35 | 95 | 200 |
| 113 | 30 | 100 | 150 |
| 114 | 30 | 90 | 100 |
| 115 | 30 | 100 | 100 |
| 116 | 30 | 100 | 100 |

Figure 8:
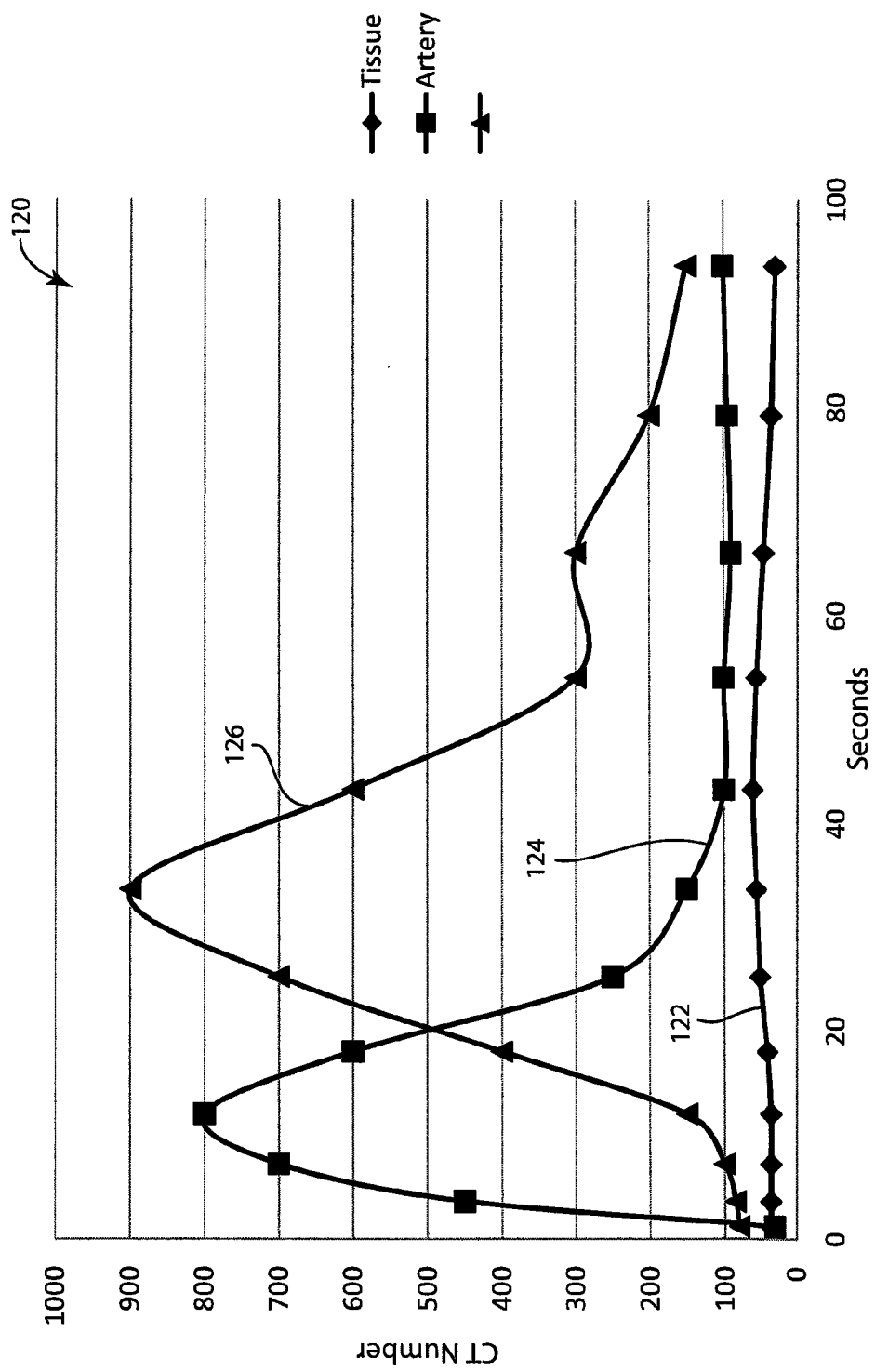
FIG. 8 is a graph depicting exemplary results from a scan of an embodiment of the perfusion phantom by a CT device.

FIG. 8 is a graph 120 that represents the CT number results of an exemplary CT scan of each of the sample rods represented in the table above. In the embodiment that resulted in the graph of FIG. 8, each of the sample cells 101-116 of the sample rod 92 is approximately one centimeter in length and the perfusion phantom 30 as described above moves the sample cells of the sample rod through the scan plane at a constant exemplary speed of 0.24 centimeters per second. Arrow 118 in FIG. 7 represents the direction of movement of the sample rod 92 through the scan plane. In an embodiment, the CT number detected by the CT device is a moving average of the CT number detected across a group of scans. It is to be understood that in modern CT devices, multiple scans are simultaneously performed on the subject. In two non-limiting examples, the CT device can simultaneously perform three scans or five scans of the subject with slightly different alignments within the scan plane.

Referring to the graph 120 of FIG. 8, the graph 120 depicts the measured CT number for a scan of each of the tissue sample rod 122, artery sample rod 124, and vein sample rod 126. As will be described in further detail herein, ideal results for the result graphs 122, 124, and 126 are known based upon the design of the specific sample rod used in the perfusion phantom 30 and the operational settings of the perfusion phantom 30. Therefore, the actual results obtained with the CT device can be compared to the known ideal scan results and adjustment or calibrations can be made to the CT device in order to achieve the known ideal scan result as the actual result. Particular deviations from the idealized graphs can be informative to skilled clinicians/technicians or analysis software in identifying the adjustment and/or correction that is required to calibrate the CT device in order to achieve the desired results.

In still further embodiments, the model CT perfusion graphs can be representative of a "normal" expected result of the perfusion of the contrast agent through the artery, vein, or tissue of the patient. The actual results performed in a CT perfusion procedure can be compared to the model graphs as obtained from a pre-procedure scan of the perfusion phantom in order to identify deviations from the actual results obtained from the patient in comparison to the model or normal expected results. This application can further assist a clinician in identifying areas of concern or abnormal perfusion procedure results.

Figure 9:
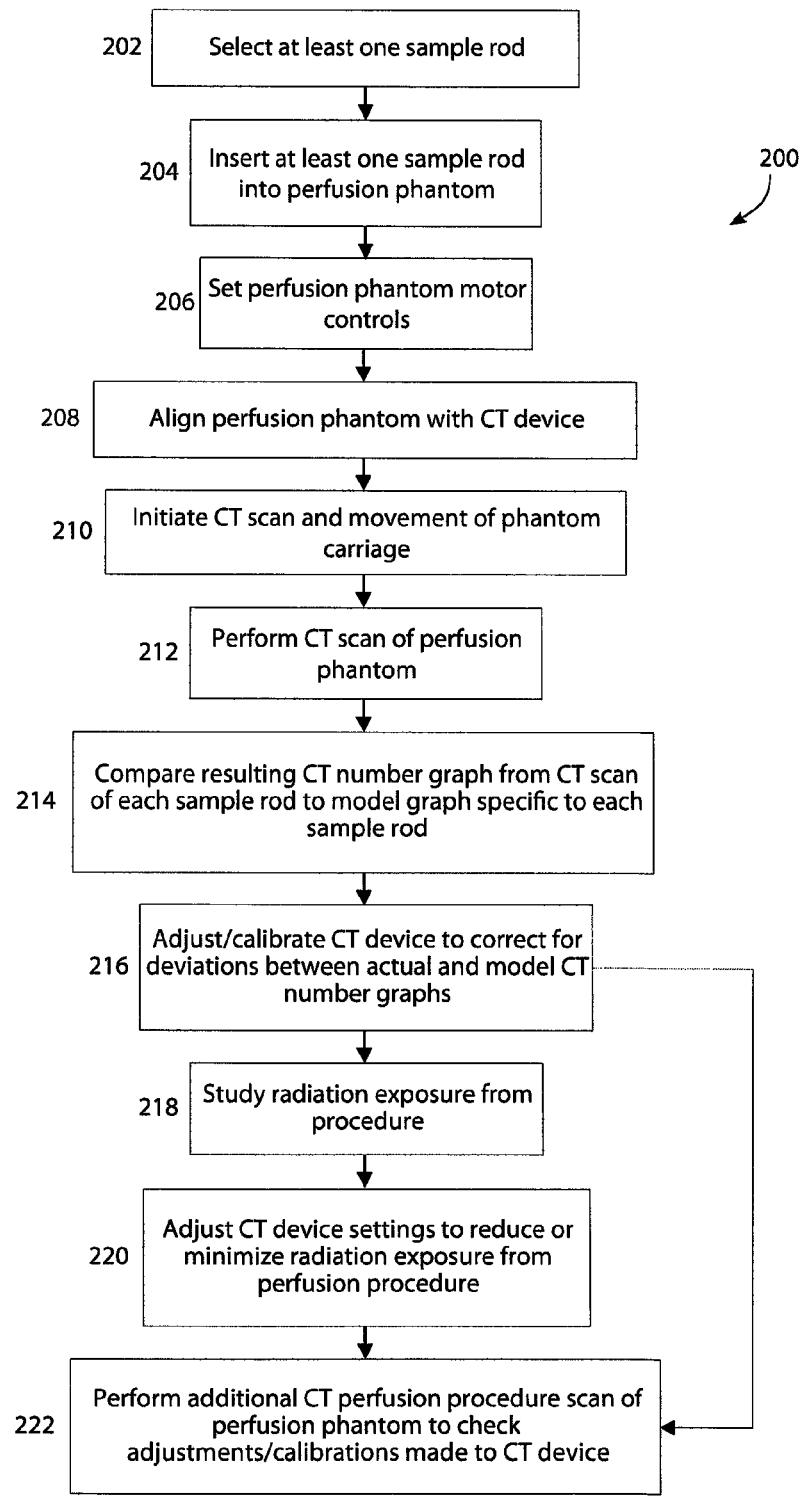
FIG. 9 is a flow chart that depicts an embodiment of a method of calibrating a CT device with an embodiment of the CT perfusion phantom.

FIG. 9 is a flow chart that depicts an embodiment of a method 200 of testing and/or calibrating a CT device for performance of a perfusion analysis procedure.

At 202, at least one sample rod is selected for use in the method 200. As disclosed above, the sample rods are constructed to each represent different vessels, tissues, organs, or organ systems to be scanned in the CT perfusion analysis procedure. Additionally, different sample rods are constructed to represent different types and concentrations of contrast agent delivered to the patient, or to represent the results of varying patient pathologies.

At least one sample rod is inserted into the perfusion phantom at 204. The perfusion phantom, as disclosed above, may include a plurality of sample tubes to receive a plurality of sample rods selected at 202. The sample tubes of the phantom may be arranged in a variety of layouts or orientations, and may exhibit different shapes, sizes, or dimensions in order to receive varying shapes, sizes, or dimensions of sample rods. Some or all of the sample tubes of the phantom may be used simultaneously as disclosed herein.

At 206, the motor controls for the perfusion phantom are set. As disclosed above, a motor in the perfusion phantom moves the carriage containing the sample rods through the scan plane of the phantom. In the exemplary embodiment above, the motor operates to drive the carriage at the rate of 0.24 centimeters per second. It is understood that in alternative embodiments, the clinician or technician performing the method 200 can control the motor of the phantom to drive the carriage at any of a variety of rates. In an alternative embodiment, the motor controls may be established to operate the motor at a variety of speeds, such that the carriage moves the sample rods through the scan plane of the phantom at varying speeds throughout the procedure, as defined in the motor controls. In a still further embodiment, the motor controls operate the motor to move the carriage such that the sample rods move back and forth through the scan plane. By adjustment of the motor controls, such as through varying routines or procedures, further bodily conditions can be represented with the perfusion phantom.

At 208, the clinician or technician aligns the perfusion phantom with the CT device. The perfusion phantom can be aligned with the CT device as disclosed above by securing the phantom to a movable gurney and operating the movable gurney to locate the perfusion phantom within the CT device. The alignment of the perfusion phantom with the CT device may include embodiments of aligning a CT imaging ROI with the perfusion phantom scan plane.

At 210, both the CT scanning procedure and the movement of the perfusion phantom carriage are initiated. In an exemplary embodiment, a coordination of the motor controller and the CT device controller is used to initiate the CT scan and the carriage movement simultaneously. In still a further embodiment, the CT scan and carriage movement are initiated in rapid succession, while in still further embodiments, a delay is incorporated into the initiation of one or more of the CT scan and carriage movement.

As disclosed above in embodiments, the CT scan is a perfusion analysis procedure which is stored as a functionality of the CT device that is carried out by operating the CT device according to stored computer programs or modules of the CT device, as disclosed above.

The CT scan of the perfusion phantom is performed at 212. If the perfusion phantom includes a plurality of sample rods as discussed above with reference to 202 and 204, the clinician or technician identifies an ROI for each of the sample rods in the captured CT images and the CT device determines a CT number of each of the ROIs in the successive CT images captured by the CT device in performing the scan of the perfusion phantom.

At 214, the resulting graph of the CT numbers for each of the sample rods is compared to a model graph that is specific to each of the sample rods and motor control settings used in the perfusion phantom. The comparison between the acquired CT numbers and the CT numbers of the model graph associated with the sample rod can be compared in a variety of ways, including, but not limited to statistical or morphological analysis of the differences between the acquired and modeled CT number graphs.

The CT device is adjusted or calibrated to correct for any identified deviation between the actual and model CT number graphs at 216. In an alternative embodiment, identification of particular deviations between the actual and model CT number graphs will indicate the need for CT device service or other condition in which the CT device should not be used for a perfusion analysis procedure. With the completion of the adjustment or calibration of the CT device 216, some embodiments of the method 200 are completed. In other embodiments, the method 200 continues to 222 where additional CT perfusion procedure scans of the perfusion phantom are performed to check and/or to recheck the adjustments or calibrations made to the CT device before the use of the CT device to perform a perfusion analysis procedure on a patient.

In another embodiment, radiation exposure from the performed CT scan is studied at 218. The radiation exposure is measured with the ion chamber included in embodiments of the perfusion phantom disclosed above. Since CT perfusion analysis procedures are a type of CT exam where one small portion of the patient's anatomy is studied over multiple scans, the target area has the potential to receive a high radiation dose. Therefore, a study of the radiation exposure at step 218 as measured by the ion chamber of the perfusion phantom enables the clinician or technician at step 220 to adjust the CT device settings to reduce or minimize radiation exposure from the perfusion procedure. The addition of the radiation exposure information as a result of conducting a CT scan of the perfusion phantom enables the clinician or technician to experiment with procedure protocols or CT device settings in order to identify or establish a protocol to deliver a minimized radiation dose while still achieving desirable CT results as identified through the comparison of the actual and model CT number graphs at 214.

Finally, at 222, additional CT perfusion procedure scans of the perfusion phantom are performed to check and/or to recheck the adjustments or calibrations made to the CT device before the use of the CT device to perform a perfusion analysis procedure on a patient.

While the invention has been described with reference to a preferred embodiment, those skilled in the art will appreciate that certain substitutions, alterations and omissions may be made without departing from the spirit thereof. Accordingly, the foregoing description is meant to be exemplary only and should not be deemed limitative on the scope of the invention set forth with the following claims.

What is claimed is:

1. A computed tomography (CT) perfusion phantom comprising:
    a scan plane configured to align with an imaging plane of a CT device;
    a plurality of sample rods that extend through the scan plane, each sample rod of the plurality includes a different plurality of adjacent cells, the plurality of adjacent cells each constructed of materials having predetermined CT numbers and the plurality of adjacent cells comprise cells of a plurality of CT numbers;
    a carriage that supports the plurality of sample rods; and
    a drive motor coupled to the carriage and the drive motor moves the carriage through the scan plane to simultaneously move the plurality of sample rods through the scan plane.

2. The CT perfusion phantom of claim 1, wherein:
    a first sample rod of the plurality of sample rods models perfusion of radiographic material into and out of an artery,
    a second sample rod of the plurality of sample rods models perfusion of radiographic material into and out of a tissue,
    a third sample rod of the plurality of sample rods models perfusion of radiographic material into and out of a vein.

3. The CT perfusion phantom of claim 1, further comprising:
    a motor controller communicatively connected to the drive motor, the motor controller operates the drive motor to move the carriage with respect to the scan plane.

4. The CT perfusion phantom of claim 3, wherein the motor controller operates the drive motor to move the carriage at a constant predetermined speed.

5. The CT perfusion phantom of claim 4, wherein the motor controller operates the drive motor to move the carriage according to a programmed protocol including varying speeds.

6. The CT perfusion phantom of claim 5, wherein the programmed protocol is coordinated with the plurality of sample rods such that the combination of the plurality of adjacent cells in the sample rods and the movement of the carriage as controlled by the motor controller simulates a perfusion of a radiographic material into and out of an anatomical structure.

7. The CT perfusion phantom of claim 1, further comprising:
    a first rail extending between the scan plane and a drive support positioned to a first side of the scan plane, and the carriage engages the first rail; and
    a second rail extending between the scan plane and a CT end handle positioned to a second side of the scan plane, the second side of the scan plane being opposed to the first side of the scan plane, and the carriage engages the second rail;
    wherein the scan plane, first rail, and second rail remain in a stationary position while the drive motor moves the carriage with respect to the scan plane, first rail, and second rail.

8. The CT perfusion phantom of claim 1, further comprising an ion chamber at least partially disposed through the scan plane.

9. The CT perfusion phantom of claim 1, wherein at least one sample rod of the plurality of sample rods models the perfusion of a radiographic material into and out of a tissue.

10. The CT perfusion phantom of claim 1, wherein at least one sample rod of the plurality of sample rods models the perfusion of a radiographic material into and out of a vessel.

11. The CT perfusion phantom of claim 1, wherein the plurality of adjacent cells are constructed of epoxy doped with varying amounts material selected from iodine and calcium.

12. A method of calibrating a computed tomography (CT) device, the method comprising:
providing a perfusion phantom comprising:
a scan plane;
a plurality of sample rods that extend through the scan plane, each sample rod of the plurality includes a different plurality of adjacent cells, the plurality of adjacent cells each constructed of materials having predetermined CT numbers and the plurality of adjacent cells comprise cells of a plurality of CT numbers;
a carriage that supports the plurality of sample rods; and
a drive motor coupled to the carriage and the drive motor moves the carriage through the scan plane;
aligning the scan plane of the perfusion phantom with an imaging plane of the CT device;
initiating a CT scan of the perfusion phantom at the scan plane with the CT device;
initiating operation of the drive motor to move the carriage and the plurality of sample rods through the scan plane oldie perfusion phantom;
acquiring a plurality of CT number measurements of the plurality of sample rods through the scan plane of the perfusion phantom;
comparing the plurality of CT number measurements to a model CT scan for each of the sample rods stored on a computer readable medium; and
calibrating the CT device based upon the comparison such that the plurality of CT number measurements match the model CT scan for each of the sample rods.

13. The method of claim 12, further comprising:
providing an ion chamber in the perfusion phantom at least partially disposed through the scan plane; and
measuring a radiation dose from the CT scan.

14. The method of claim 13, wherein the CT scan is performed by the CT device according to a perfusion procedure and the method further comprises modifying the perfusion procedure to minimize a radiation dose from the perfusion procedure.

15. The method of claim 12, wherein a first sample rod of the plurality of sample rods models perfusion of a radiographic substance through a vessel and a second sample rod of the plurality of sample rods models perfusion of a radiographic substance through a tissue.

16. The method of claim 15, wherein the first sample rod of the plurality of sample rods models perfusion through an artery and a third sample rod of the plurality of sample rods models perfusion through a vein.

17. The method of claim 12, further comprising:
providing a plurality of sample rods, each sample rod of the plurality modeling perfusion through a different anatomical structure;
selecting a sample rod from the plurality of sample rods based upon an anatomical structure of a patient to be imaged; and
inserting the sample rod into the perfusion phantom.

18. The method of claim 17 wherein each sample rod of the plurality is configured with a different plurality of adjacent cells.

19. The method of claim 12, wherein the perfusion phantom includes a motor controller and the method further comprises operating the drive motor with the motor controller to move the sample rod according to a programmed protocol.

20. The method of claim 12, further comprising:
simulating perfusion of radiographic material through an anatomical structure by operation of the drive motor;
wherein a first sample rod of the plurality of sample rods models perfusion of radiographic material through a tissue, a second sample rod of the plurality of sample rods models perfusion of radiographic material through an artery, and a third sample rod of the plurality of sample rods models perfusion of radiographic material through a vein.

* * * * *